United States Patent
Nelvig

(10) Patent No.: US 8,298,397 B2
(45) Date of Patent: Oct. 30, 2012

(54) AUXILIARY DEVICE, A MARINE SURFACE VESSEL, AND A METHOD FOR CORROSION PROTECTION IN A MARINE CONSTRUCTION

(75) Inventor: Carl Nelvig, Göteborg (SE)

(73) Assignee: AB Volvo Penta, Göteborg (SE)

( * ) Notice: Subject to any disclaimer, the term of this patent is extended or adjusted under 35 U.S.C. 154(b) by 146 days.

(21) Appl. No.: 12/996,022

(22) PCT Filed: Jun. 25, 2008

(86) PCT No.: PCT/SE2008/000410
§ 371 (c)(1),
(2), (4) Date: Dec. 3, 2010

(87) PCT Pub. No.: WO2009/157816
PCT Pub. Date: Dec. 30, 2009

(65) Prior Publication Data
US 2011/0083973 A1    Apr. 14, 2011

(51) Int. Cl.
C23F 13/04    (2006.01)
C23F 13/20    (2006.01)
C23F 13/22    (2006.01)

(52) U.S. Cl. ........ 205/740; 205/725; 205/727; 205/730; 204/196.37; 204/196.02; 204/196.04; 204/196.06; 204/196.07; 204/196.1; 307/95

(58) Field of Classification Search .................. 205/725, 205/727, 730, 740; 204/196.02, 196.04, 204/196.06, 196.07, 196.1, 196.37; 307/95
See application file for complete search history.

(56) References Cited

U.S. PATENT DOCUMENTS

| 2,918,420 | A | | 12/1959 | Sabins |
| 5,627,414 | A | * | 5/1997 | Brown et al. ............... 205/726 |
| 6,183,625 | B1 | * | 2/2001 | Staerzl ...................... 205/727 |
| 7,381,312 | B1 | * | 6/2008 | Misorski et al. ......... 204/196.18 |
| 8,118,983 | B1 | * | 2/2012 | Anderson et al. ........ 204/196.11 |

FOREIGN PATENT DOCUMENTS

GB    868810 A    5/1961

OTHER PUBLICATIONS

International Search Report for corresponding International Application PCT/SE2008/000410.
International Preliminary Report on Patentability for corresponding International Application PCT/SE2008/000410.

* cited by examiner

Primary Examiner — Bruce Bell
(74) Attorney, Agent, or Firm — WRB-IP LLP

(57) ABSTRACT

A method for corrosion protection in a marine construction including a plurality of metal elements and at least one reference electrode at least partly immersed in water, the metal elements including an anode and a metal part, the anode being provided for corrosion protection of the metal part includes measuring an electric potential of the metal part with the reference electrode as a ground reference. At least one of the metal elements and at least one of the at least one reference electrode are connected to a DC electrical power outlet so as to allow an electrical regeneration current through an electrical circuit including the at least one of the metal elements, the at least one of the at least one reference electrode and the electrolyte so that the reference electrode is anodized.

23 Claims, 10 Drawing Sheets

AUXILIARY DEVICE, A MARINE SURFACE VESSEL, AND A METHOD FOR CORROSION PROTECTION IN A MARINE CONSTRUCTION

BACKGROUND AND SUMMARY

The present invention relates to an auxiliary device, a marine surface vessel, and a method for corrosion protection in a marine construction, such as a marine surface vessel or a marine structure, the marine construction comprising a plurality of metal elements and at least one reference electrode, the metal elements and the reference electrode being at least partly immerged in an electrolyte in the form of water, in which the marine construction is at least partially immerged, the metal elements comprising an anode and a metal part, the anode being provided for corrosion protection of the metal part by the provision of an electrical protection current through an electrical circuit comprising the anode, the metal part and the electrolyte, the method comprising measuring an electric potential of the metal part with the reference electrode as a ground reference.

In marine constructions, such as marine vessels and marine structures; a known way to protect an immersed metal part against galvanic corrosion is to provide a sacrificial anode, made of very pure zinc, magnesium, cast iron or an alloy of aluminum, which is directly fastened to, or electrically connected via a cable to the immersed metal part. In such a system, herein referred to as a passive corrosion protection system, or simply a passive system, the sacrificial anode will waste away, preventing damage to the immersed metal part. An alternative to passive arrangements with sacrificial anodes is impressed current cathodic protection (ICCP) systems. In such a system, one or more active anodes are immersed and connected along with the immersed metal part to a common DC electrical power source. ICCP system active anodes usually have tubular or solid rod shapes, or are provided as continuous ribbons, and can include materials such as titanium, platinum, high silicon cast iron, graphite, mixed metal oxide, and niobium. Regardless whether the corrosion protection system is a passive system or of the ICCP type, a circuit is provided by an electrical current through the water serving as an electrolyte, and a surface polarization at the interface between the metal part and the water is created, serving to protect the metal part against corrosion.

In a passive system, as well as in an ICCP system, for a good corrosion protection, the electrical current between the anode and the metal part should be such that the surface polarization of the metal part is kept close to a desired value, or a desired interval, which depends on the material of the metal part. If said current is too low, the protection is too low, and the metal part may corrode at an undesired rate. For some metals, e.g. aluminum, damages can occur also if the current is too high. In general, too high of a current between the anode and the metal part gives calcium oxide precipitation which can stimulate excessive growth of sea weeds and sea animals on the metal part. Such growth is a particularly large concern in the case of recreational boats, which often stay docked giving opportunities for the growth.

ICCP systems usually include an electronic control unit (ECU) by means of which the electrical current between the anode and the metal part can be varied and controlled, which allows for control of the current between the anode and the metal part through the electrolyte, and thereby control of the surface polarization at an interface between the metal part and the electrolyte. Also passive systems can include such control, which can be obtained by an adjustable resistance in the electrical connection between the sacrificial anode and the metal part, for example as described in U.S. Pat. No. 5,627,414.

The control of the current is carried out based on measurements of a parameter indicative of said polarization. Such measurements are obtained by means of a reference electrode also immersed in the electrolyte. More specifically, the ECU is adapted to measure an electrical potential of the metal part with the reference electrode as a ground reference, and to control the current between the anode and the metal part based on these measurements and the desired value, or desired interval, of the electrical potential of the metal part with the reference electrode as a ground reference. This desired value, or desired interval, depends on a number of circumstances, for example, the type of reference electrode used, and the type of electrolyte. As an example, where the metal part is made of a material from a certain group of copper alloys, and the electrolyte is salt water, the desired value of the electrical potential of the metal part with a silver chloride coated silver reference electrode as a ground reference is suitably within the interval −450 mV-(−600) mV. As a further example, where the same type of reference electrode is used in the same type of electrolyte, and the metal part is made of a material from a certain group of aluminum alloys, the desired value of the electrical potential of the metal part with the reference electrode as a ground reference is suitably −950 mV.

A problem with silver chloride coated silver reference electrodes, below also referred to as silver/silver chloride reference electrodes, is that the silver chloride coating thereof can be partially or completely lost for example by physical wear, and/or by polarization due to an external electrical field. This problem is also present at reference electrodes with an electrically conductive core, for example a copper core, a silver layer outside the core and a silver chloride layer outside the silver layer, below referred to as core/silver/silver chloride reference electrodes. A possible reason for reference electrode damage on recreational boats is the use, while the boat is lifted, of high pressure washers, the jet of which can remove the silver chloride coating of exposed reference electrodes. The electrical potential measurement provided with a reference electrode on which the silver chloride coating is partially or completely lost will be inaccurate, and the measured value will differ from the value that would have been obtained with an intact reference electrode. In turn this will provide an erroneous input for the control of the electrical current between the anode and the metal part, resulting in a less than optimal corrosion protection, and possibly even damage to the metal part.

For boats, a known measure for taking care of damaged reference electrodes is the obvious one of lifting the boat, and replacing the electrodes, which of course involves the need for expensive replacement electrodes, and adds to the maintenance of the boat.

It is desirable to improve the corrosion protection in marine constructions.

It is also desirable to reduce errors in the measurement of the electrical potential of a metal part with a reference electrode as a ground reference in a marine construction.

It is a further desirable to provide an accurate corrosion protection in marine constructions, while keeping maintenance of the marine construction low.

According to an aspect of the present invention, a method comprises connecting at least one of the metal elements and at least one of the at least one reference electrode to a DC electrical power source so as to allow an electrical regeneration current through an electrical circuit comprising the at least one of the metal elements, the at least one of the at least one reference electrode and the electrolyte, so as for the reference electrode to be anodized.

By the method according to an aspect of the invention, a regeneration of the reference electrode will provided by it being anodized, which in the case of silver/silver chloride reference electrodes or core/silver/silver chloride reference electrodes will reestablish damaged or worn off silver chloride layers. This in turn will eliminate the risk of erroneous inputs for the corrosion protection, securing an accurate protection. Also, such reference electrode regeneration can be carried out at any time while the marine construction is in its normal immersed state, without the need for time consuming and expensive maintenance, such as lifting a boat and replacing the electrodes.

It should be noted that for proper anodizing of the reference electrode, it should be connected to a positive pole of the DC electrical power source and the metal element should be connected to a negative pole of the DC electrical power source. It should also be noted that the metal element forming a part of the electrical circuit for anodizing the reference electrode does not necessarily have to be identical with the metal part that is to be protected from corrosion. For example, the at least one of the metal elements, connected along with the at least one of the at least one reference electrode to the DC electrical power source so as to allow the electrical regeneration current, can be the anode provided for corrosion protection of the metal part. Thereby, the anode can be an active anode provided for impressed current cathodic protection of the metal part, or a sacrificial anode in a passive system. However, in a preferred embodiment, the at least one of the metal elements, connected along with the at least one of the at least one reference electrode to the DC electrical power source so as to allow the electrical regeneration current, is the metal part for which the anode is provided for corrosion protection.

It should further be noted that the invention is applicable to any corrosion protection system where reference electrodes are used to measure the surface polarization of the metal part to be protected, regardless whether the system is active or passive. In addition, it should be noted that since the invention concerns marine constructions, the electrolyte is sea water, i.e. salt water, brackish water or freshwater. As exemplified below, the DC electrical power outlet can be fed from a separate DC electrical power source, or it can be identical with a DC electrical power source.

Preferably, the method comprises measuring separately the electric potential of one of the metal elements with a respective of at least two reference electrodes as a ground reference, and connecting at least one of the metal elements and at least one of the reference electrodes to the DC electrical power source, if the electrical potential measured with one of the reference electrodes differs substantially from the electrical potential measured with another of the reference electrodes.

This given a secure manner to establish whether there is a need for regeneration of any of the reference electrodes. For example, where the corrosion protection system comprises two reference electrodes, and the electrical potential of the metal part is measured with each of the two reference electrodes as a ground reference, if the electrical potential measured with one of the reference electrodes differs substantially from the electrical potential measured with the other reference electrode, this is an indication that at least one of the reference electrodes is defective. Thereby, both reference electrodes can be connected to the positive pole of the DC electrical power source, so as for them to be anodized.

It should be noted that, notwithstanding that the reference electrodes are used to measure the electric potential of the metal part provided with corrosion protection, the step mentioned above of measuring the electric potential can also be seen as a calibration measure for the reference electrodes, and as such it can involve measuring the electric potential of the metal part provided with corrosion protection, or any other metal element of the marine construction. For example, in a passive system, a metal element used for such a calibration measure can be the sacrificial anode. However, in an ICCP system, the active anode is often not suitable to be used as a metal element for a calibration measure of said type since it is usually electrically charged.

Preferably, the step of connecting at least one of the metal elements and at least one of the reference electrodes to the DC electrical power source is carried out if the electrical potential measured with one of the reference electrodes differs from the electrical potential measured with another of the reference electrodes by at least a predetermined threshold value. Where two reference electrodes are used the difference electrical potential measurements is easy to establish. In systems with three reference electrodes, the measurement difference compared to the predetermined threshold value can either be the difference between the highest and the lowest measured values, or the largest difference between two measured values without any measured value between them. The latter alternative provides a narrower limit for the divergence between the measured values.

Preferably, the predetermined threshold value is at least 5 mV. Thereby, preferably the measurement difference compared to the predetermined threshold value is the largest difference between two measured values without any measured value between them. Specifically, the predetermined threshold value can be in the interval 5-100 mV. In more preferred embodiments, the predetermined threshold value can be in the interval 5-75 mV, advantageously in the interval 20-50 mV.

Preferably, the method comprises measuring separately the electric potential of one of the metal elements with a respective of three reference electrodes as a ground reference, and connecting, if the electrical potential measured with one of the reference electrodes differs substantially from the electrical potentials measured with the two other reference electrodes, at least one of the metal elements and the reference electrode, with which the substantially differing electric potential was measured, to the DC electrical power source.

An advantage with using three reference electrodes in this manner is that if only one of the reference electrodes is defective and needs to be regenerated, this reference electrode can be identified. This means that only the reference electrode identified as defective needs to be subjected to the step mentioned above so as to be anodized. As an example, the method can comprise measuring the electrical potential of the metal part with a first, a second and a third reference electrode as ground references, and connecting, if the electrical potential measured with the first reference electrode differs substantially from the electrical potentials measured with the second and third reference electrodes, the first reference electrode to the positive pole of the DC electrical power source, so as for it to be anodized.

Also, in certain applications, carrying out on one of the three reference electrodes the regeneration might have to be followed by a time period during which a remaining electric potential of the reference electrode, caused by the regeneration, decreases, before the reference electrode is used for measurements in the corrosion protection system. During this time period the other two reference electrodes may be used for measurements in the system.

It should be noted that where a plurality of reference electrodes are used as stated above, they should be galvanically separated from each other.

Alternatively, the method can comprise performing repetitively, at predetermined time intervals, the step of connecting the at least one of the metal elements and the at least one of the at least one reference electrode to the DC electrical power source. Thereby, the corrosion protection can be carried out with only one reference electrode. In addition, instead of being used for total renovation of a malfunctioning silver/silver chloride reference electrode or core/silver/silver chloride reference electrode, the method can be used for maintaining such a reference electrode, by carrying out the regeneration relatively often. Thereby, the regeneration can be carried out during a relatively short time, for example once a week for 30 seconds, or once a month for one minute. Below, some advantageous values for the current density during the regeneration are given.

Preferably, the method comprises controlling the electrical regeneration current through the electrical circuit comprising the at least one of the metal elements, the at least one of the at least one reference electrode and the electrolyte. Since a correct level of the regeneration current is important for the anodizing process of the reference electrode, by such current control it is possible to secure a successful result of the regeneration. Preferably, said electrical regeneration current is controlled by control of a variable resistance in said electrical circuit.

Preferably, the electrical regeneration current is such that the current density at the reference electrode is 0.1-250 mA/cm2, in more preferred embodiments 0.1-100 mA/cm2, in yet even more preferred embodiments 1-40 mA/cm2. In particularly preferred embodiments said current density is 3-18 mA/cm2. In this current density interval the marine construction corrosion protection reference electrode will be regenerated at current density levels provided by tests presented in "Reference electrodes: Theory and practice", David J G Ives & George J Janz, Academic Press, New York 1961. In mostly preferred embodiments said current density is 5-12 mA/cm2.

The current density at the reference electrode is the electrical regeneration current divided by the surface area of the reference electrode. It should be noted that said current density values are suitable for a silver/silver chloride reference electrode, or a core/silver/silver chloride reference electrode. The current density can be controlled for example as mentioned above, i.e. by controlling the electrical regeneration current by control of a variable resistance in said electrical circuit. Alternatively, the current density can be controlled by controlling the electrical tension (voltage) between the metal element and the reference electrode.

In embodiments mentioned above, where more than one reference electrode is provided, and the electrical potential measured with one of the reference electrodes differs substantially from the electrical potential measured with another of the reference electrodes, the regeneration might be carried out in order to provide a total renovation of one or more of the electrodes. Such a total renovation might of course also be carried out where only one reference electrode is provided. Suitably, if a total renovation is desired, the regeneration is carried out at said current density values, preferably at 3-18 mA/cm2, during 2-30 minutes. A test performed by the inventor suggested that a regeneration at a current density of 5-12 mA/cm2, preferably approximately 8 mA/cm2 during approximately 15 minutes provides a very good result. In general, if a relatively high current density is provided, the duration of the regeneration can be relatively short, and vice versa. However, the use of current densities that are too high, or regeneration durations that are too long, might provide a silver chloride layer that easily releases from the silver core, (or the silver layer provided on the electrically conductive core).

DESCRIPTION OF THE FIGURES

Below, the invention will be described in detail with reference to the drawings, in which.

DETAILED DESCRIPTION

Figure 1:
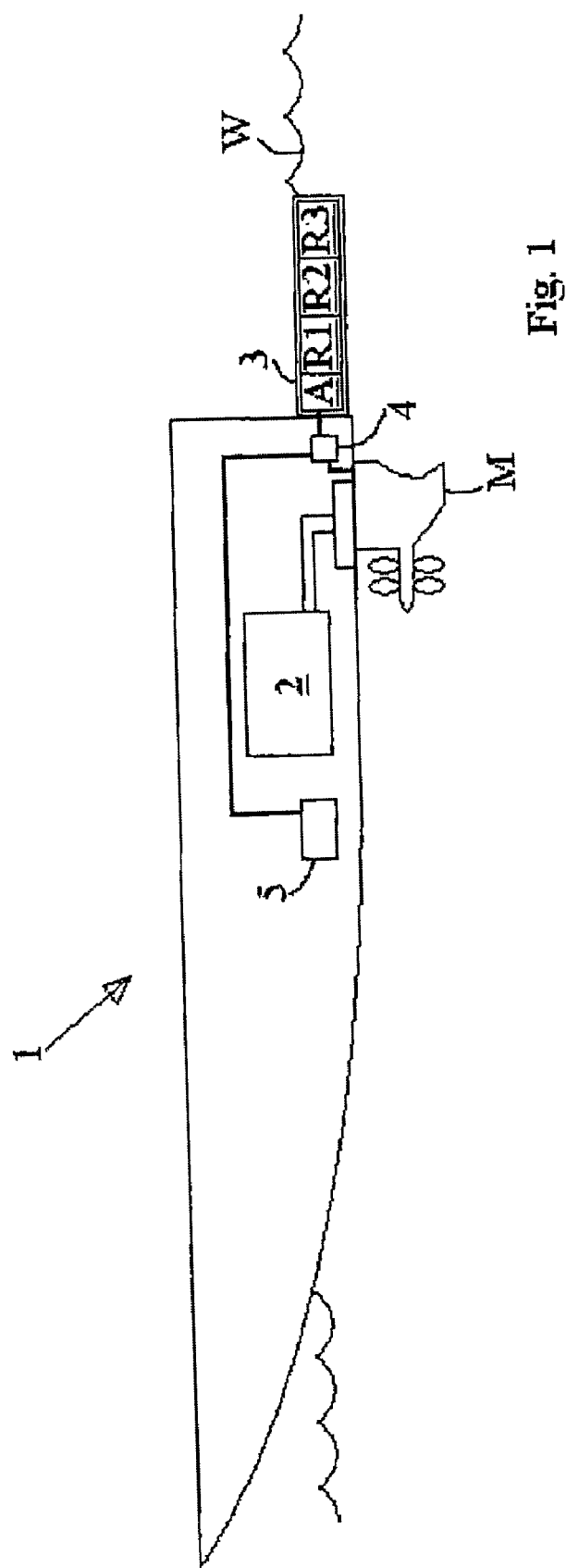
FIG. 1 shows a schematic cross-sectional side view of a boat.

FIG. 1 shows a schematic cross-sectional side view of a boat 1 with a corrosion protection system in turn comprising an impressed current cathodic protection (ICCP) system. The boat 1 is provided with an engine 2 connected to a drive M, with propellers for the propulsion of the boat. In this example, the drive M, immerged in the water W, constitutes a metal part to be protected by the corrosion protection system. In FIG. 1, the drive M is schematically presented as a drive manufactured and marketed by Volvo Penta as an IPS (Inboard Performance System) drive, but the invention is of course applicable to boats with any kind of drive, for example a stern drive or a traditional propeller and rudder combination. Also, the invention is applicable to boats with any number of engines and drives.

Figure 2:
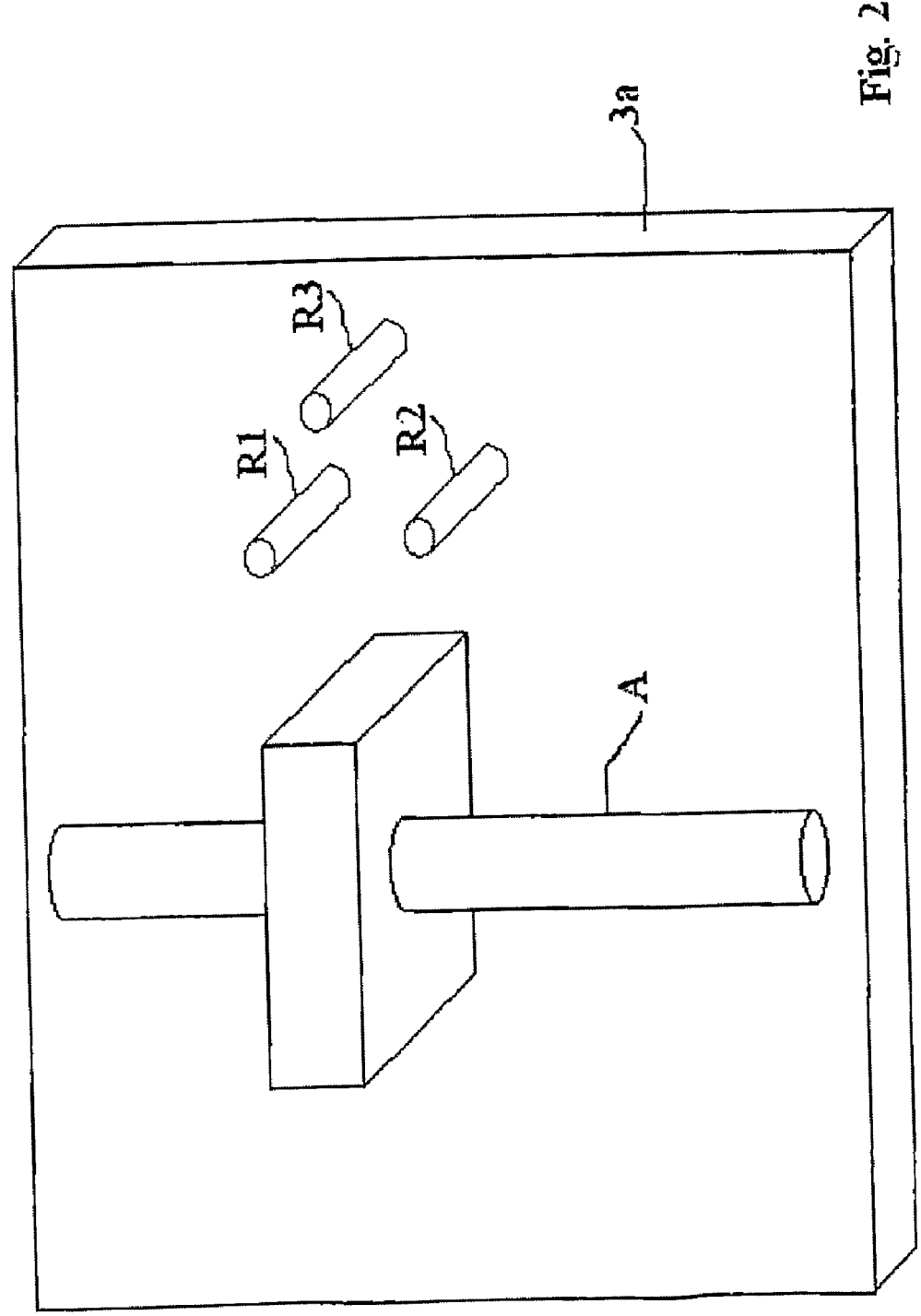
FIG. 2 is a schematic perspective view of a back wall of an external unit for a corrosion protection system of the boat in FIG. 1.

Reference is also made to FIG. 2. The corrosion protection system comprises an external unit 3, mounted on a transom of the boat 1. FIG. 2 shows a back wall 3 *a* of the external unit 3, more specifically a side of the back wall 3 *a* facing inwards in the external unit 3. The external unit 3 is adapted to be immerged in the water, and comprises an active anode A, which is provided in the form of a MMO (mixed metal oxide) coated titanium rod mounted on the back wall 3 *a*. More generally, the anode A can be provided as one or more platinum coated titanium rods, or MMO (mixed metal oxide) coated anodes. Alternative shapes for the active anode A include tubular shapes and shapes as continuous ribbons, and alternative materials include high silicon cast iron, graphite and niobium. The external unit 3 also comprises three reference electrodes R1, R2, R3, herein referred to as a first, second and third reference electrode R1, R2, R3. The reference electrodes are supplied in the form of solid rods made of silver coated with silver chloride. Alternatively, the above mentioned core/silver/silver chloride reference electrodes can be provided.

It should be noted that in alternative embodiments, the active anode A and the reference electrodes R1, R2, R3 can be provided in separate units.

Referring again to FIG. 1, the corrosion protection system also comprises an electronic control unit (ECU) 4, to which the drive M, the active anode A, and the reference electrodes R1, R2, R3 are connected. Also, an electrical power source 5, in the form of a 12 volt DC battery, is connected to the ECU 4. Of course, the DC battery could be provided with other voltage levels, e.g. 24 volts.

Figure 3:
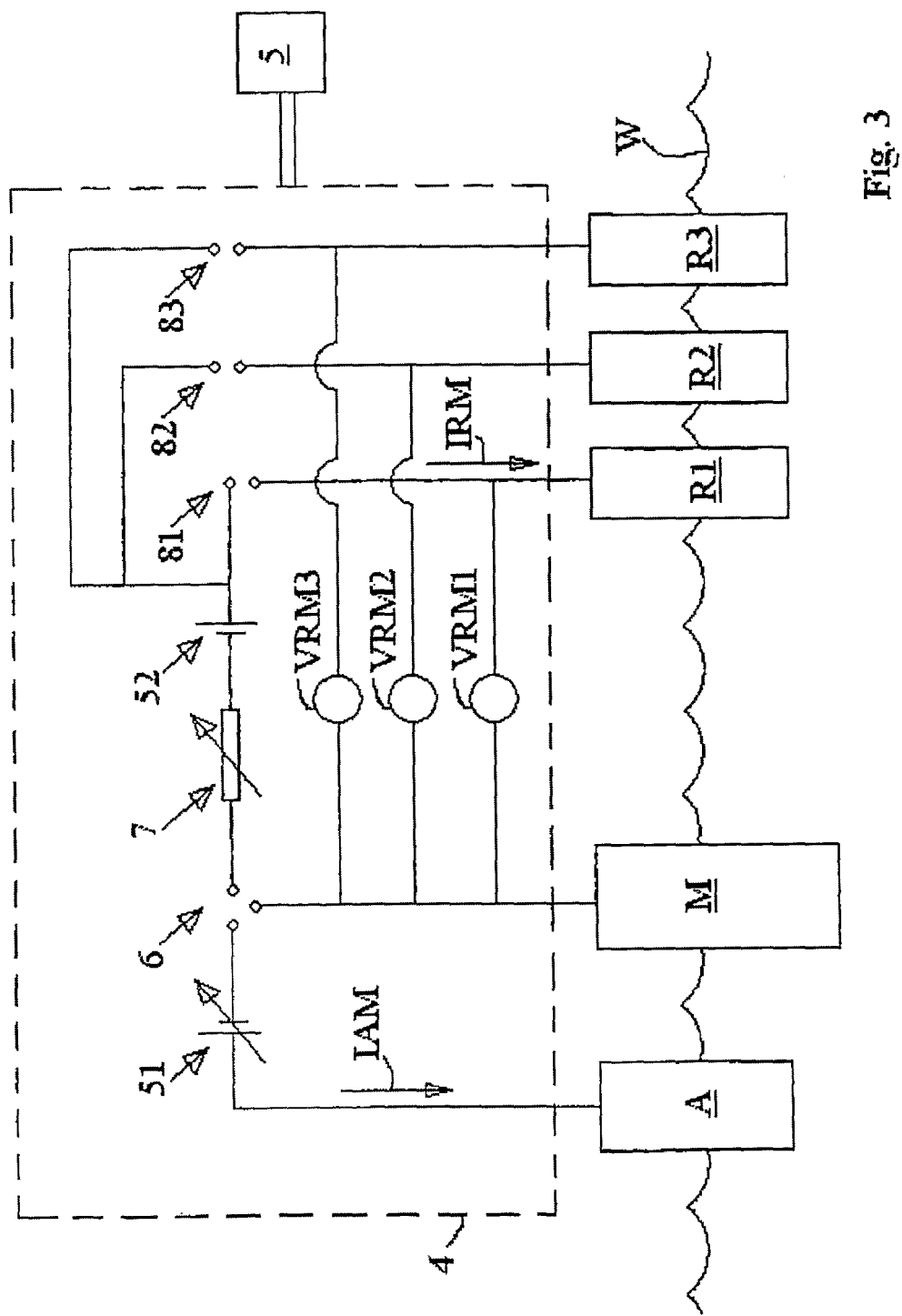
FIG. 3 shows, with parts represented as blocks, a depiction of the corrosion protection system of the boat in FIG. 1.

FIG. 3 shows a schematic representation of the corrosion protection system of the boat in FIG. 1. A switch, herein referred to as a mode switch 6, is controllable by the ECU 4, and can be set so that the battery 5 is connected to, and adapted to provide DC electrical power to the active anode A and the drive M via a first power outlet 51.

The ECU 4 is adapted to provide a first measurement VRM1 of the electrical potential of the drive M with the first reference electrode R1 as a ground reference, a second measurement VRM2 of the electrical potential of the drive M with the second reference electrode R2 as a ground reference, and a third measurement VRM3 of the electrical potential of the drive M with the third reference electrode R3 as a ground reference. If all reference electrodes are functioning properly, the first, second and third electrical potential measurements VRM1, VRM2, VRM3 are substantially the same.

The ECU 4 is further adapted to control the electrical power to the active anode A and the drive M (as indicated with the sign in FIG. 3 at the arrow 51) based on the electrical potential measurements VRM1, VRM2, VRM3, so as to provide a desired surface polarization of the drive M, in order to provide a proper corrosion protection. Thereby, the electric potential measurements VRM1, VRM2, VRM3 are indicative of the surface polarization of the drive M. The corrosion protection is provided by an electrical current, herein also referred to as an electrical protection current IAM5 through an electrical circuit comprising the active anode A, the drive M and the water W.

The silver chloride coating of the reference electrodes R1, R2, R3 can be partially or completely lost for example by physical wear, and/or by polarization due to an external electrical field. The electrical potential measurement VRM1, VRM2, VRM3 provided with a reference electrode R1, R2, R3 on which the silver chloride coating is partially or completely lost will be inaccurate, and the measured value will differ from the actual electrical potential.

As can be seen in FIG. 3, the system comprises further switches, herein referred to as a first, a second and a third reference switch 81, 82, 83, which are controllable by the ECU 4. By means of the mode switch 6, the drive M can be disconnected from the first power outlet 51, and instead be connected to the negative pole of a second power outlet 52. Also, by means of the reference switches 81, 82, 83, one or more of the reference electrodes R1, R2, R3 can be connected to the positive pole of the second power outlet 52. Thereby the battery 5 can be connected to, and adapted to provide DC electrical power to one or more of the reference electrodes R1, R2, R3 and the drive M via a second power outlet 52. It should be noted that alternatively, the first and second power outlets 51, 52 can be provided by separate DC power sources.

According to this embodiment of the invention, if the first measurement VRM1 differs substantially from the second and third measurements VRM2, VRM3, the following actions are taken: The drive M is disconnected from the first power outlet 51, and is instead connected to the negative pole of a second power outlet 52, and the first reference switch 81 is controlled so that the first reference electrode R1 is connected to the positive pole of the second power outlet 52, so as to allow an electrical current, herein also referred to as an electrical regeneration current IRM through an electrical circuit comprising the reference electrode R1, the drive M and the water W, so as for the first reference electrode R1 to be anodized, at which the drive M assumes the function of a cathode.

More specifically, the steps mentioned so as to anodize the first reference electrode R1 are carried out if the first measurement VRM1 differs from any of the simultaneously provided second and third measurements VRM2, VRM3 by more a predetermined threshold value. In this example, this predetermined threshold value is 30 mV.

It should be noted that said predetermined threshold value is the absolute value of any calculated difference. In the following two examples, it is assumed that the drive M is made in a copper alloy, for which the desired value of the surface polarization for corrosion protection is −450 mV. If the electrical potential measurements VRM1, VRM2, VRM3 are simultaneously provided, and the first, the second and third electrical potential measurements VRM1, VRM2, VRM3 are −415 mV, −448 mV and −451 mV, respectively, the second smallest difference between the three electrical potential measurements is |−415−(−448)|=33 mV, which is larger than the predetermined threshold value. In another example, if the first, the second and third electrical potential measurements VRM1, VRM2, VRM3 are −483 mV, −448 mV and −451 mV, respectively, the second smallest difference between the three electrical potential measurements is |−483−(−451)|=32 mV, which is also larger than the predetermined threshold value.

During the anodizing of the first reference electrode R1, at which the drive M is connected to the negative pole of a second power outlet 52, and the first reference electrode R1 is connected to the positive pole of the second power outlet 52, the regenerating current through the reference electrode R1, the drive M and the water W is carefully controlled by means of an adjustable resistance 7, in this example provided in the connection between the drive M and the second power outlet 52.

Figure 4:
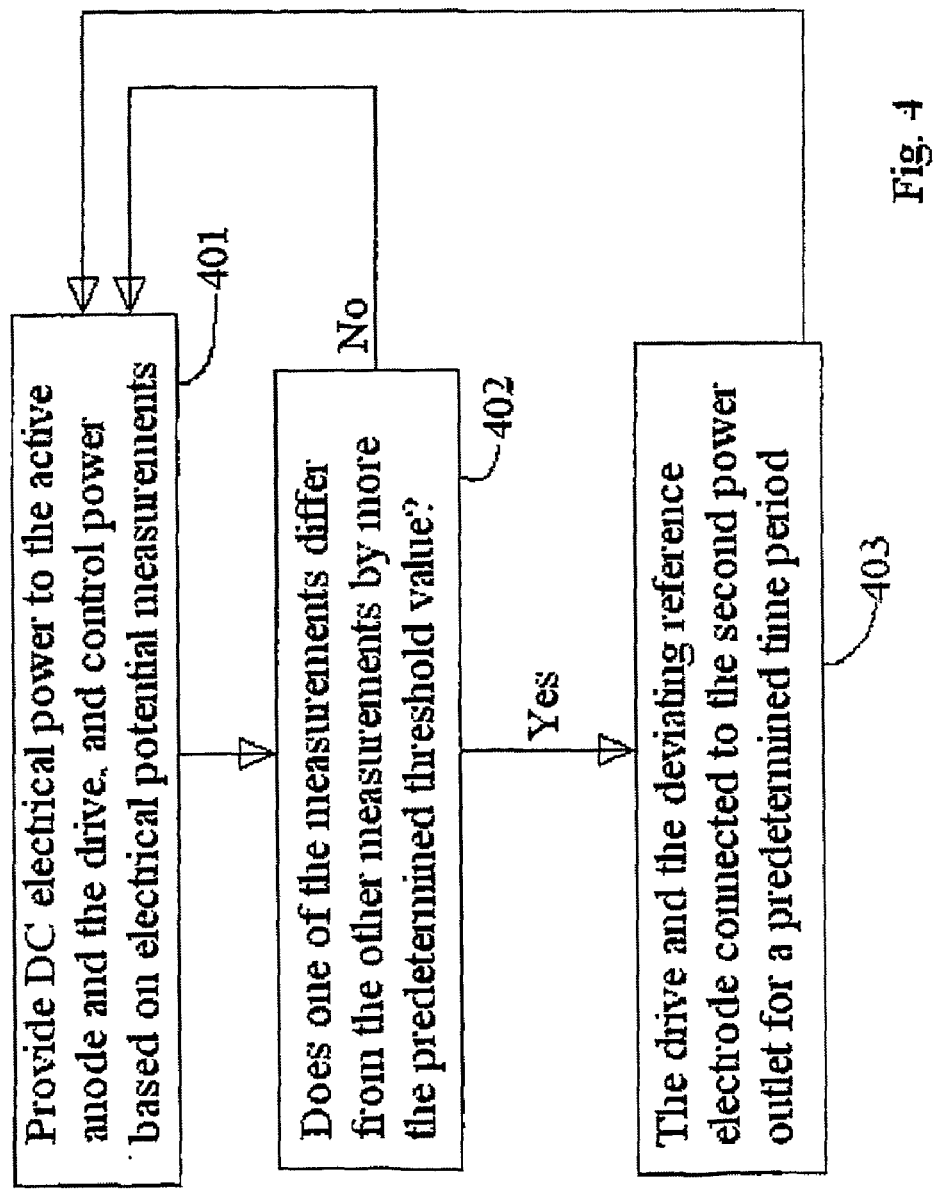
FIG. 4 shows a block diagram depicting steps in a method according to the preferred embodiment of the invention.

FIG. 4 depicts steps in the method according to the preferred embodiment of the invention. In a normal corrosion protection mode, DC electrical power is provided 401 to the active anode A and the drive M via a first power outlet 51, and controlled based on the measurements VRM1, VRM2, VRM3 of the electrical potential of the drive M with the reference electrodes R1, R2, R3 as ground references. During the corrosion protection mode, the ECU 4 compares the measurements VRM1, VRM2, VRM3 to each other, and determines 402 whether any of them differs from any of the other measurements by more the predetermined threshold value. If it is determined that one of the measurements VRM1, VRM2, VRM3 differs from the other measurements by more the predetermined threshold value, the drive M is disconnected from the first power outlet 51, and instead connected to the negative pole of the second power outlet 52, and the reference electrode, by which the measurement differing from the other measurements by more than the threshold value was obtained, is connected 403 to the positive pole of the second power outlet 52. After a predetermined time period, the reference electrode anodizing measure 403 is terminated, and DC electrical power is again provided 401 to the active anode A and the drive M via a first power outlet 51.

In an alternative embodiment, if it is determined 402 within a short time period after the reference electrode anodizing measure 403 that the reference electrode having been subjected to said measure 403 still gives an electrical potential measurement that deviates by more than a predetermined value, the other two reference electrodes are subjected to the anodizing measure 403. The reason is that in such a case it can be suspected that the other two reference electrodes are malfunctioning.

Nevertheless, preferably, during the anodizing measure 403, electrical power is still provided to the active anode A and the drive M via the first power outlet 51, and controlled based on the measurements of the electrical potential of the drive M with the reference electrodes not subjected to the anodizing measure 403 as ground references.

It should be noted that in alternative embodiments, during the reference electrode anodizing measure, a metal element other than the drive M, for example a zink sacrificial anode, can be connected to the negative pole of the second power outlet 52. In case of a zink sacrificial anode being connected in this manner, this will allow an electrical regeneration current IRM through an electrical circuit comprising the reference electrode R1, the zink sacrificial anode and the water W, so as for the first reference electrode R1 to be anodized, at which the zink sacrificial anode assumes the function of a cathode.

Figure 5:
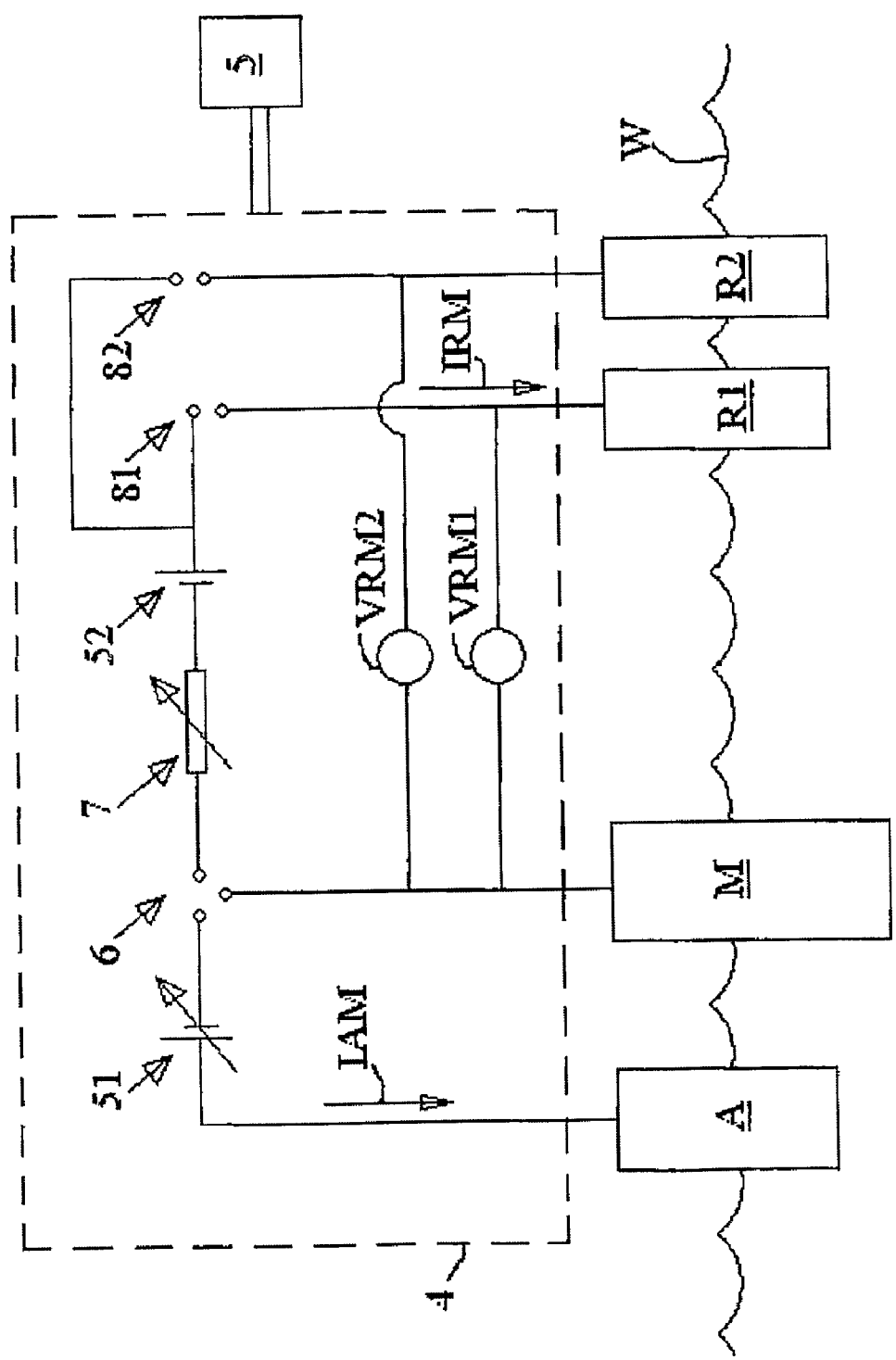
FIG. 5-FIG. 8 show, with parts represented as blocks, depictions of corrosion protection systems according to alternative embodiments of the invention.

FIG. 5 depicts a corrosion protection system according to an alternative embodiment of the invention, similar to the one described above with reference to FIG. 1-FIG. 4, but with the following exception. In the system in FIG. 5, only two reference electrodes R1, R2 are provided. During a normal corrosion protection mode, the electrical potential of the drive M is measured with each of the two reference electrodes R1, R2 as a ground reference. If the electrical potential measurements provided by the reference electrodes differs from each other, by more than a predetermined threshold value, both reference electrodes are connected to the second power outlet 52, so as for them to be anodized.

Still referring to FIG. 5, in an alternative embodiment, the reference electrodes are anodized sequentially one at a time. Whether or not both electrodes are anodized simultaneously, during the anodizing measure(s), electrical power can still be provided to the active anode A and the drive M via the first power outlet 51. Thereby, the electrical power to the active anode A and the drive M can be constant at a level which is determined before the anodizing measure(s).

Figure 6:
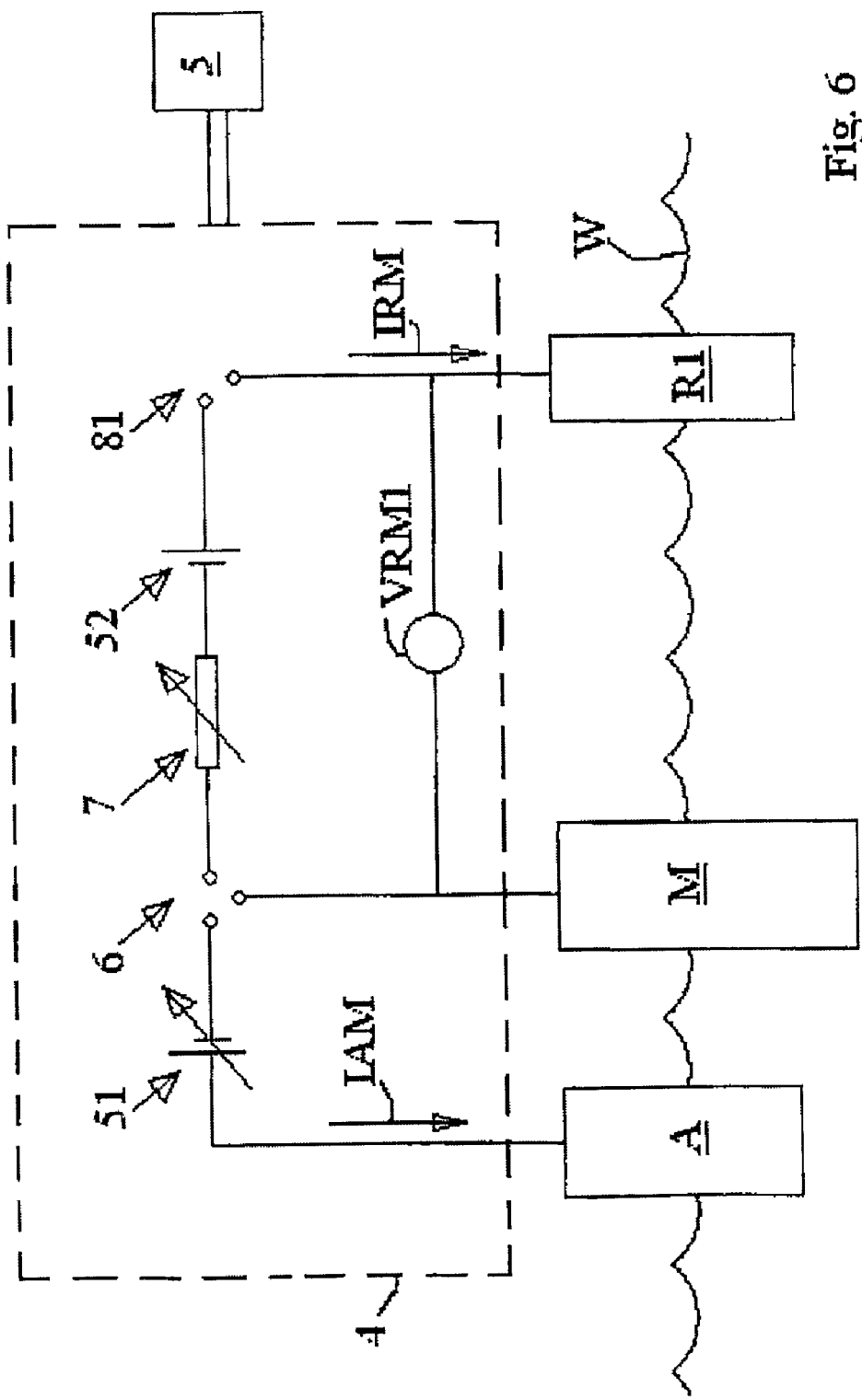

FIG. 6 depicts a corrosion protection system according to a further alternative of the invention, similar to the one described above with reference to FIG. 5, but with the following exception. In the system in FIG. 6, only one reference electrode R1 is provided. During a normal corrosion protection mode, the electrical potential of the drive M is measured with the reference electrode R1 as a ground reference. At predetermined repeated time intervals, the reference electrode is connected to the second power outlet 52, so as for it to be anodized.

Figure 7:
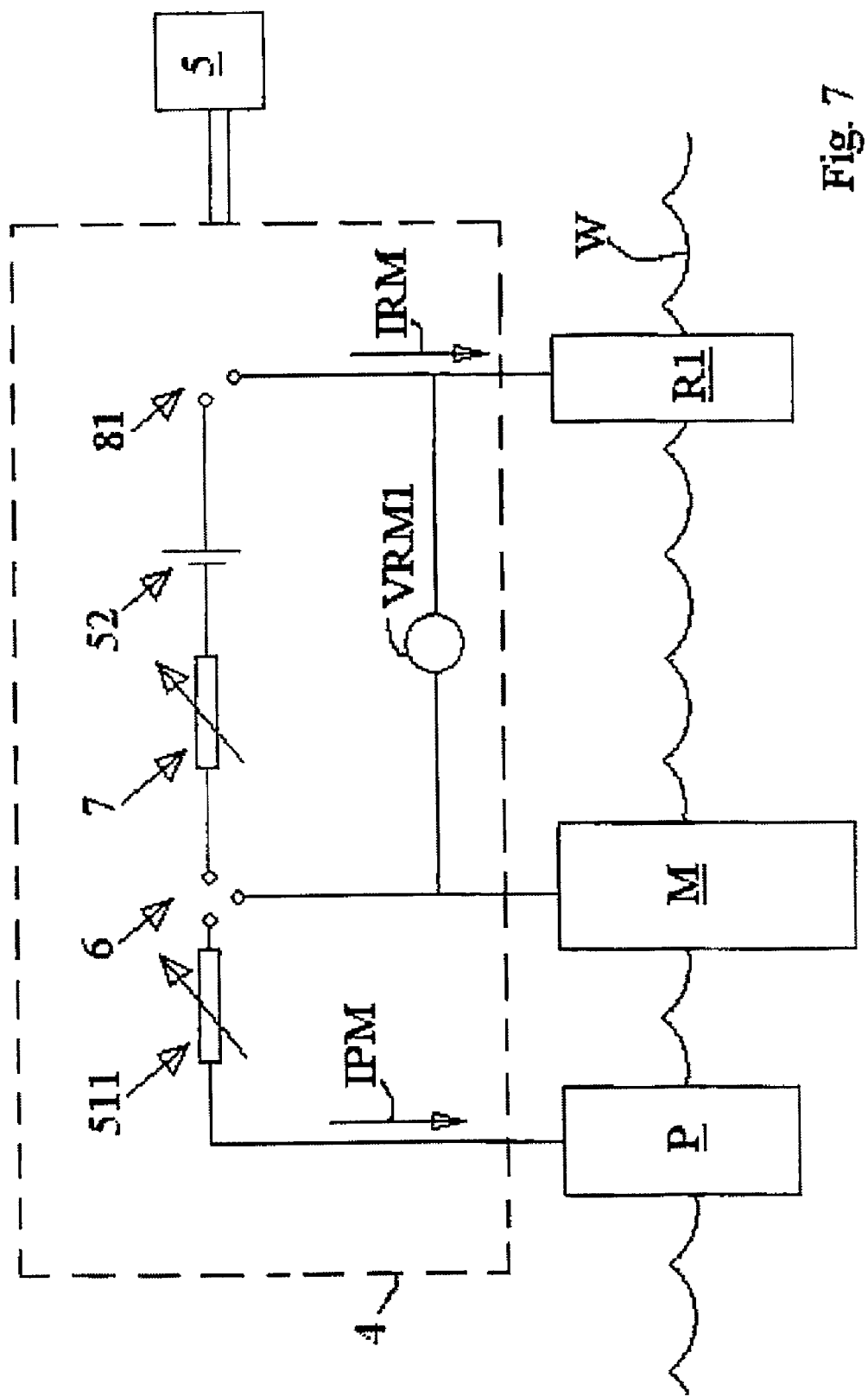

FIG. 7 depicts a corrosion protection system according to another embodiment of the invention, similar to the one described above with reference to FIG. 6, but with the following exceptions. In the system in FIG. 7, the anode is a passive anode P, herein also referred to as a sacrificial anode P. An electrical protection current IPM through an electrical circuit comprising the sacrificial anode P, the drive M and the electrolyte is controlled by means of a further adjustable resistance 511 provided in said circuit, which control is based on measurements of the electrical potential of the drive M with the reference electrode R1 as ground reference.

It should be noted that the mode switch 6 can in certain embodiments be adapted to be controlled manually. Also, it is possible to provide the corrosion protection system without an adjustable resistance 7, at which the regenerating current through the reference electrode R1, the drive M and the water W is predetermined. Thereby, the second power outlet 52 can be identical with the DC electrical power source 5.

Figure 8:
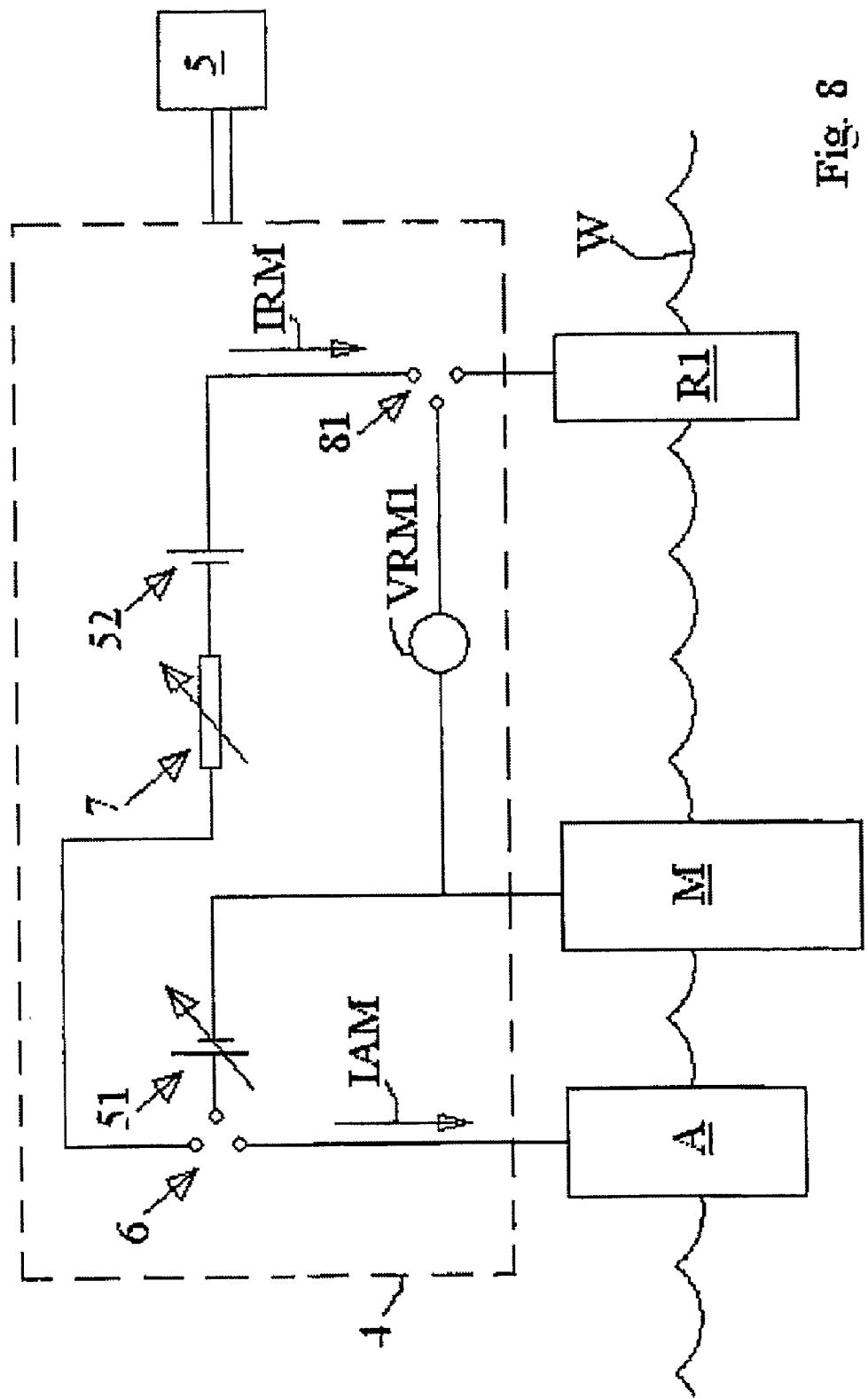

FIG. 8 depicts a corrosion protection system according to a further alternative embodiment of the invention, similar to the one described above with reference to FIG. 6, but with the following exception. For anodizing the reference electrode R1, the active anode A is, by control of a switch 6, disconnected from the first power outlet 51, and is instead connected to the negative pole of the second power outlet 52, and a further switch 81 is controlled so that the reference electrode R1 is connected to the positive pole of the second power outlet 52, so as to allow an electrical regeneration current IRM through an electrical circuit comprising the reference electrode R1, the active anode A and the water W, at which the active anode A assumes the function of a cathode.

Figure 9:
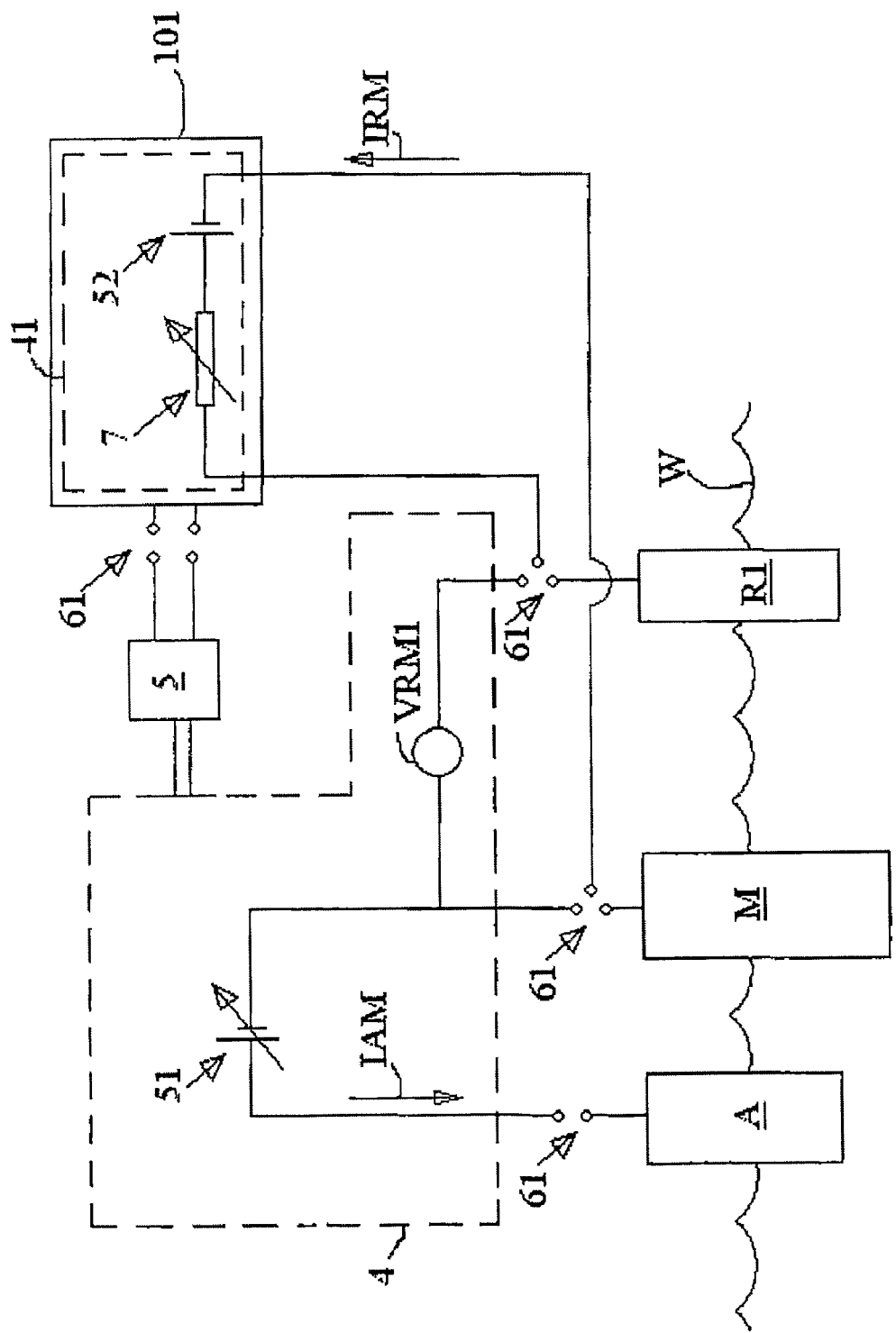
FIG. 9 and FIG. 10 show, with parts represented as blocks, depictions of corrosion protection systems with respective auxiliary devices according to respective embodiments of the invention.

FIG. 9 depicts a corrosion protection system according to yet another embodiment of the invention. A boat 1 (not shown) is provided with an ICCP system, and an engine (not shown) connected to a drive M protected by the ICCP system. The ICCP system comprises an active anode A, and a reference electrode R1. The ICCP system also comprises an ECU 4, to which the drive M, the active anode A, and the reference electrode R1 are connected. Also, an electrical power source 5, in the form of a DC battery, is connected to the ECU 4.

A separate auxiliary device 101, which is adapted to be transported by a person, is adapted to be manually connected to the battery 5, the reference electrode R1 and the drive M. More specifically, terminals 61 are provided to disconnect the active anode A from the ECU 4, i.e. from the battery 5, and to connect the battery 5, the reference electrode R1 and the drive M to the auxiliary device 101. Thereby, the auxiliary device 101 provides a connection of the drive M and the reference electrode R1 to a DC electrical power source 52 in the auxiliary device 101, in turn fed from the battery 5. This connection allows an electrical regeneration current IRM through an electrical circuit comprising the drive M, the reference electrode R1 and the water W, so as for the reference electrode R1 to be anodized.

The auxiliary device 101 comprises an ECU 41, adapted to control, during the anodizing of the reference electrode R1, the regenerating current by means of an adjustable resistance 7, and to terminate the anodizing measure after a predetermined time interval. Alternatively, the auxiliary device 101 can be adapted for the anodizing measure to be terminated by an operator, at which the ECU 41 can be omitted.

As an alternative, the metal element used for the regeneration of the reference electrode R1 could be, instead of the drive M, the active anode.

Figure 10:
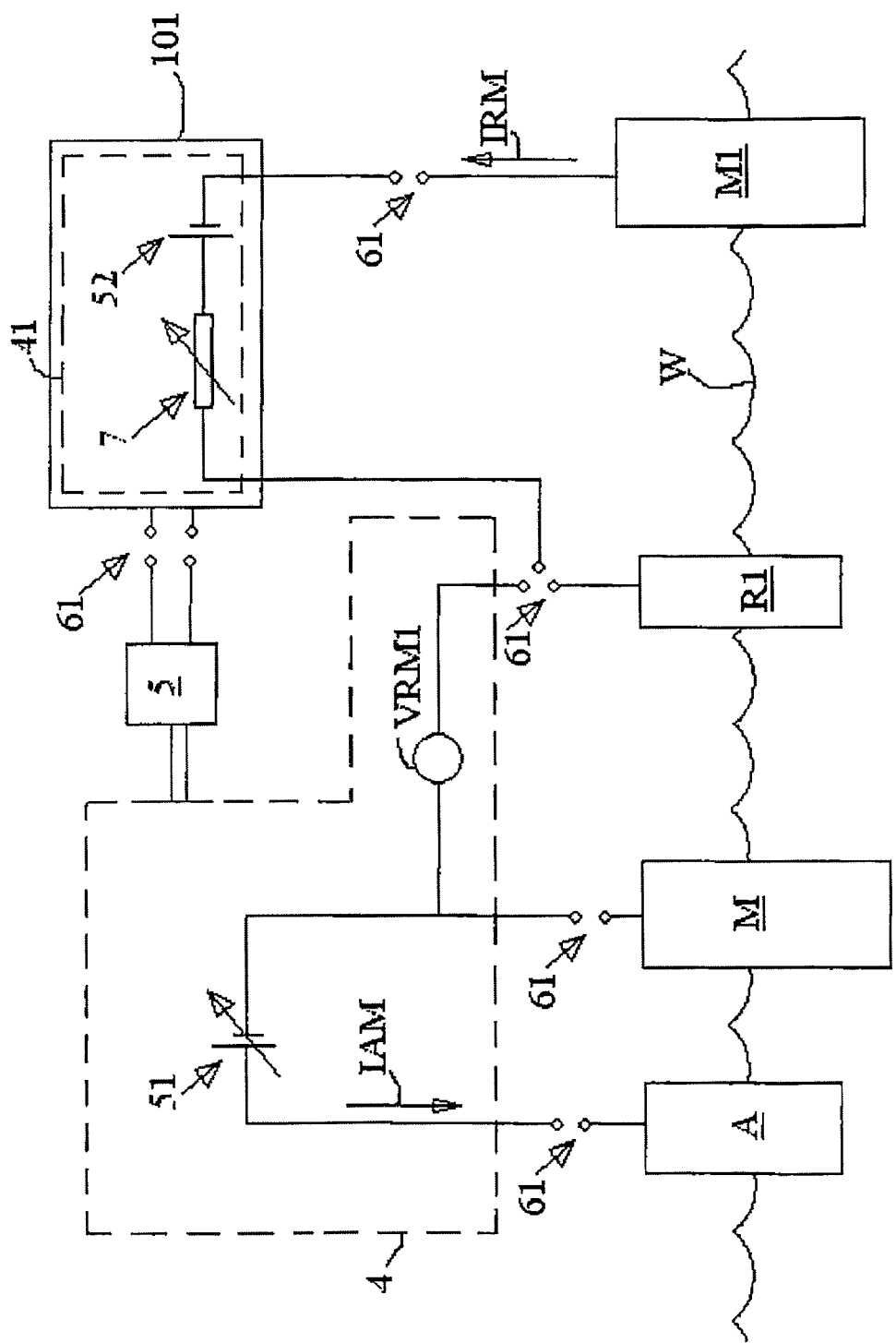

FIG. 10 depicts a corrosion protection system according to a further embodiment of the invention, similar to the one shown in FIG. 9, but with the following exception: The auxiliary device 101 is adapted to be manually connected to the battery 5, the reference electrode R1 and a metal element M1 immersed in the water. More specifically, terminals 61 are provided to disconnect the active anode A and the drive M from the ECU 4, i.e. from the battery 5, and to connect the battery 5, the reference electrode R1 and the drive M to the auxiliary device 101. Thereby, the auxiliary device 101 provides allowing an electrical regeneration current IRM through an electrical circuit comprising the metal element M1, the reference electrode R1 and the water W, so as for the reference electrode R1 to be anodized.

It should be noted that the metal element M1 could be any metal element, for example one that is mounted on the boat and immersed in the water while the boat is in the water. Alternatively, the metal element M1 used for the regeneration of the reference electrode R1 could be included in the auxiliary device 101 and adapted to be submerged in the water particularly for the regeneration.

It should also be noted that in alternative embodiments, a separate battery 5 could be included in the auxiliary device.

The invention claimed is:

1. A method for corrosion protection in a marine construction, such as a marine surface vessel or a marine structure, the marine construction comprising a plurality of metal elements and at least two reference electrodes, the metal elements and the reference electrodes being at least partly immersed in an electrolyte in the form of water, in which the marine construction is at least partially immersed, the metal elements comprising an anode and a metal part, the anode being provided for corrosion protection of the metal part by the provision of an electrical protection current through an electrical circuit comprising the anode, the metal part and the electrolyte, the method comprising:
measuring an electric potential of the metal part with the reference electrode as a ground reference,
connecting at least one of the metal elements and at least one of the at least one reference electrode to a DC electrical power outlet so as to allow an electrical regeneration current through an electrical circuit comprising the at least one of the metal elements the at least one of the at least one reference electrode and the electrolyte, so as for the reference electrode to be anodized,
measuring separately the electric potential of one of the metal elements with a respective of at least two reference electrodes as a ground reference, and connecting at least one of the metal elements and at least one of the reference electrodes to the DC electrical power outlet, if the electrical potential measured with one of the reference electrodes differs substantially from the electrical potential measured with another of the reference electrodes.

2. A method according to claim 1, wherein the at least one of the metal elements, connected along with the at least one of the at least one reference electrode to the DC electrical power outlet so as to allow the electrical regeneration current, is the metal part for which the anode is provided for corrosion protection.

3. A method according to claim 1, wherein the at least one of the metal elements (M, A, P, M1), connected along with the at least one of the at least one reference electrode to the DC electrical power outlet so as to allow the electrical regeneration current, is the anode provided for corrosion protection of the metal part.

4. A method according to claim 1, wherein the step of connecting at least one of the metal elements and at least one of the reference electrodes to the DC electrical power outlet is carried out if the electrical potential measured with one of the reference electrodes differs from the electrical potential measured with another of the reference electrodes by at least a predetermined threshold value.

5. A method according to claim 4, wherein the predetermined threshold value is at least 5 mV.

6. A method according to claim 1, comprising measuring separately the electric potential of one of the metal elements with a respective of three reference electrodes as a ground reference, and connecting, if the electrical potential measured with one of the reference electrodes differs substantially from the electrical potentials measured with the two other reference electrodes, at least one of the metal elements and the reference electrode, with which the substantially differing electric potential was measured, to the DC electrical power outlet.

7. A method according to claim 1, comprising performing repetitively, at predetermined time intervals, the step of connecting the at least one of the metal elements and the at least one of the at least one reference electrode to the DC electrical power outlet.

8. A method according to claim 1, comprising controlling the electrical regeneration current through the electrical circuit comprising the at least one of the metal elements, the at least one of the at least one reference electrode and the electrolyte.

9. A method according to claim 8, wherein the electrical regeneration current is controlled by control of a variable resistance in the electrical circuit.

10. A method according to claim 1, wherein the electrical regeneration current is such that the current density at the reference electrode is 0.1-250 mA/cm2.

11. A marine surface vessel comprising
a plurality of metal elements and at least two reference electrodes, the metal elements and the reference electrodes being adapted to be at least partly immersed in an electrolyte in the form of water, in which the marine surface vessel is at least partially immersed, the metal elements comprising an anode and a metal part, the anode being provided for corrosion protection of the metal part by the provision of an electrical protection current through an electrical circuit comprising the anode the metal part and the electrolyte, the reference electrodes being adapted to be used as a ground reference when measuring an electric potential of the metal part, wherein at least one of the metal elements and at least one of the at least two reference electrodes are connectable to a DC electrical power outlet so as to allow an electrical regeneration current through an electrical circuit comprising the at least one of the metal elements, the at least one of the at least two reference electrodes and the electrolyte, so as for the reference electrode to be anodized, and
an electronic control unit adapted to allow connection of the at least one of the metal elements and of at least one of the reference electrodes to the DC electrical power outlet, if the electrical potential of one of the metal elements measured with one of the reference electrodes differs substantially from the electrical potential of the metal element measured with another of the reference electrodes.

12. A marine surface vessel according to claim 11, wherein the at least one of the metal elements, connectable along with the at least one of the at least one reference electrode to the DC electrical power outlet so as to allow the electrical regeneration current, is the metal part for which the anode is provided for corrosion protection.

13. A marine surface vessel according to claim 11, wherein the at least one of the metal elements, connectable along with the at least one of the at least one reference electrode to the DC electrical power outlet so as to allow the electrical regeneration current, is the anode provided for corrosion protection of the metal part.

14. A marine surface vessel according to claim 11, wherein the electronic control unit is adapted to allow connection of the at least one of the metal elements and of at least one of the reference electrodes to the DC electrical power outlet if the electrical potential measured with one of the reference electrodes differs from the electrical potential measured with another of the reference electrodes by at least a predetermined threshold value.

15. A marine surface vessel according to claim 11, comprising three reference electrodes and an electronic control unit adapted to allow connection, if the electrical potential of one of the metal elements measured with one of the reference electrodes differs substantially from the electrical potentials of the metal element measured with the two other reference electrodes, of at least one of the metal elements and of the reference electrode, with which the substantially differing electric potential was measured, to the DC electrical power outlet.

16. A marine surface vessel according to claim 11, comprising an electronic control unit adapted to allow repetitively, at predetermined time intervals, connection of the at least one of the metal elements (M, A, P, M1) and of the at least one of the at least one reference electrode to the DC electrical power outlet.

17. A marine surface vessel according to claim 11, comprising an electronic control unit adapted to control the electrical regeneration current through the electrical circuit comprising the at least one of the metal elements, the at least one of the at least two reference electrodes and the electrolyte.

18. A marine surface vessel according to claim 17, wherein the electronic control unit is adapted to control the electrical regeneration current by control of a variable resistance in the electrical circuit.

19. A marine surface vessel according to claim 1, comprising an electronic control unit adapted to control the electrical regeneration current such that the current density at the reference electrode is 0.1-250 mA/cm2.

20. An auxiliary device, it is adapted to provide a connection from a DC electrical power outlet to at least one of a plurality of metal elements, and to at least one of at least two reference electrodes of a marine construction, such as a marine surface vessel or a marine structure, the metal elements and the reference electrodes being at least partly immersed in an electrolyte (W) in the form of water, in which the marine construction (1) is at least partially immersed, the metal elements comprising an anode and a metal part, the anode being provided for corrosion protection of the metal part by the provision of an electrical protection current (IAM, IPM) through an electrical circuit comprising the anode, the metal part and the electrolyte, the reference electrodes being adapted to be used as a ground reference when measuring an electric potential of the metal part, the connection of the DC electrical power outlet to at least one of the metal elements and to the at least one of the at least two reference electrodes allowing an electrical regeneration current through an electrical circuit comprising the at least one of the metal elements, the at least one of the at least two reference electrodes and the electrolyte, so as for the reference electrodes to be anodized.

21. An auxiliary device according to claim 20, comprising an electronic control unit adapted to control the electrical regeneration current.

22. An auxiliary device according to claim 21, wherein the electronic control unit is adapted to control the electrical regeneration current by control of a variable resistance in the electrical circuit.

23. An auxiliary device according to claim 20, comprising an electronic control unit adapted to control the electrical regeneration current such that the current density at the reference electrode is 0.1-250 mA/cm2.

* * * * *